(12) United States Patent
Banko (10) Patent No.: US 11,207,212 B2
(45) Date of Patent: Dec. 28, 2021

(54) PHACO CONE WORK TIP FOR A SURGICAL HAND-PIECE

(71) Applicant: SURGICAL DESIGN CORPORATION, Armonk, NY (US)

(72) Inventor: William Banko, Armonk, NY (US)

(73) Assignee: SURGICAL DESIGN CORPORATION, Armonk, NY (US)

( * ) Notice: Subject to any disclaimer, the term of this patent is extended or adjusted under 35 U.S.C. 154(b) by 133 days.

(21) Appl. No.: 15/941,366

(22) Filed: Mar. 30, 2018

(65) Prior Publication Data

US 2019/0117458 A1    Apr. 25, 2019

(51) Int. Cl.
*A61F 9/007* (2006.01)
*A61B 17/32* (2006.01)
*A61M 3/02* (2006.01)

(52) U.S. Cl.
CPC .. *A61F 9/00745* (2013.01); *A61B 17/320068* (2013.01); *A61B 2017/32007* (2017.08); *A61B 2017/320074* (2017.08); *A61B 2017/320075* (2017.08); *A61B 2017/320084* (2013.01); (Continued)

(58) Field of Classification Search
CPC ..... A61F 9/00745; A61B 2017/320069; A61B 2017/32007; A61B 2017/320071; A61B 2017/320072; A61B 2017/320082; A61B 2017/320084; A61B 2017/320088; A61B 2017/320089; A61B 2017/320093; A61B 2017/320094; A61B 2017/320095; A61B 2017/320097; A61B 2017/320098; A61B 17/320068; A61B 17/320092; A61B 2018/00595; A61B 2018/00577; A61B 2018/0063; A61B 2018/00601; A61B 2018/00589; A61B 2217/005; (Continued)

(56) References Cited

U.S. PATENT DOCUMENTS 4,320,761 A * 3/1982 Haddad ............... A61F 9/00763
                                                  408/58
5,254,082 A    10/1993  Takase
5,359,996 A    11/1994  Hood
(Continued)

FOREIGN PATENT DOCUMENTS

DE  10 2015 207 150 A1   11/2016
WO  WO 2008/118709 A1    10/2008

OTHER PUBLICATIONS

U.S. Appl. No. 15/783,806, filed Oct. 13, 2017, Banko.
(Continued)

*Primary Examiner* — Katherine M Rodjom
(74) *Attorney, Agent, or Firm* — Leason Ellis LLP (57) ABSTRACT

A work tip for a surgical hand piece has a solid knife connected to a source of ultrasonic energy in the hand piece and a sleeve having a generally uniform cylindrical shape that surrounds the distal end of the knife. The distal end of the knife has at least a portion of a conical tip, e.g., a Cobra tip. The sleeve provides irrigation and aspiration fluid channels. Also, a structure in the sleeve blocks the proximal opening in the upper part of the conical tip when the knife is withdrawn into the sleeve. A hole is provided in the sleeve adjacent to, but proximally of the structure so that when a portion of the opening is blocked, aspiration fluid flows through the hole to provide I/A clean up.

21 Claims, 12 Drawing Sheets

(52) U.S. Cl.
CPC ... *A61B 2217/005* (2013.01); *A61B 2217/007* (2013.01); *A61M 3/0283* (2013.01)

(58) Field of Classification Search
CPC .. A61B 2217/007; A61B 2017/320074; A61B 2017/320075; A61M 3/0283
USPC .................................. 606/169, 179; 604/22
See application file for complete search history.

(56) References Cited

U.S. PATENT DOCUMENTS

| | | | | |
|---|---|---|---|---|
| 5,693,062 | A * | 12/1997 | Stegmann | A61F 9/00763 604/22 |
| 5,695,461 | A | 12/1997 | Shaible | |
| 5,709,698 | A * | 1/1998 | Adams | A61B 17/32002 604/22 |
| 6,592,541 | B1 * | 7/2003 | Kurwa | A61F 9/00745 604/22 |
| 8,951,272 | B2 * | 2/2015 | Robertson | A61B 17/32002 606/169 |
| 2002/0111608 | A1 | 8/2002 | Baerveldt et al. | |
| 2003/0229344 | A1 | 12/2003 | Dycus et al. | |
| 2005/0049546 | A1 | 3/2005 | Messerly et al. | |
| 2011/0196399 | A1 | 8/2011 | Robertson et al. | |
| 2014/0163595 | A1 | 6/2014 | Witt et al. | |
| 2014/0276369 | A1 | 9/2014 | Banko | |
| 2014/0277030 | A1 * | 9/2014 | Lauchner | A61B 17/1671 606/169 |
| 2015/0126994 | A1 | 5/2015 | Matsui et al. | |

OTHER PUBLICATIONS

New Phaco Tip Geometry Balances Power, Suction, *Ophthalmology Times*, Jul. 15, 1992, vol. 17, No. 14, 3 pages.
Funnel-shaped tip Controls Ultrasound Energy during Phaco, *Ocular Surgery News*, Jul. 1, 1992, vol. 10, No. 13, 2 pages.
International Search Report and Written Opinion in corresponding PCT Application No. PCT/US2019/024910, dated Jun. 24, 2019.
International Search Report and Written Opinion in corresponding PCT Application No. PCT/US2020/012388, dated Apr. 20, 2020.
International Preliminary Report on Patentability PCT Application No. PCT/US2019/024910, dated Oct. 6, 2020.
International Preliminary Report on Patentability in corresponding PCT Application No. PCT/US 2020/012388, dated Jun. 16, 2021.
International Search Report and Written Opinion in corresponding PCT Application No. PCT/US2020/054389, dated Feb. 4, 2021.

* cited by examiner

PHACO CONE WORK TIP FOR A SURGICAL HAND-PIECE

TECHNICAL FIELD

The present invention is generally directed to work tips for surgical hand pieces, particularly work tips with cone shapes for use in the removal of cataracts from the eye of a patient by phacoemulsification.

BACKGROUND OF THE INVENTION

The use of instruments in ocular surgical applications is well known. One widely used type of instrument is an ultrasonic hand piece that is used in ophthalmic applications, such as in the removal of cataracts from the eye by phacoemulsification.

Figure 1A:
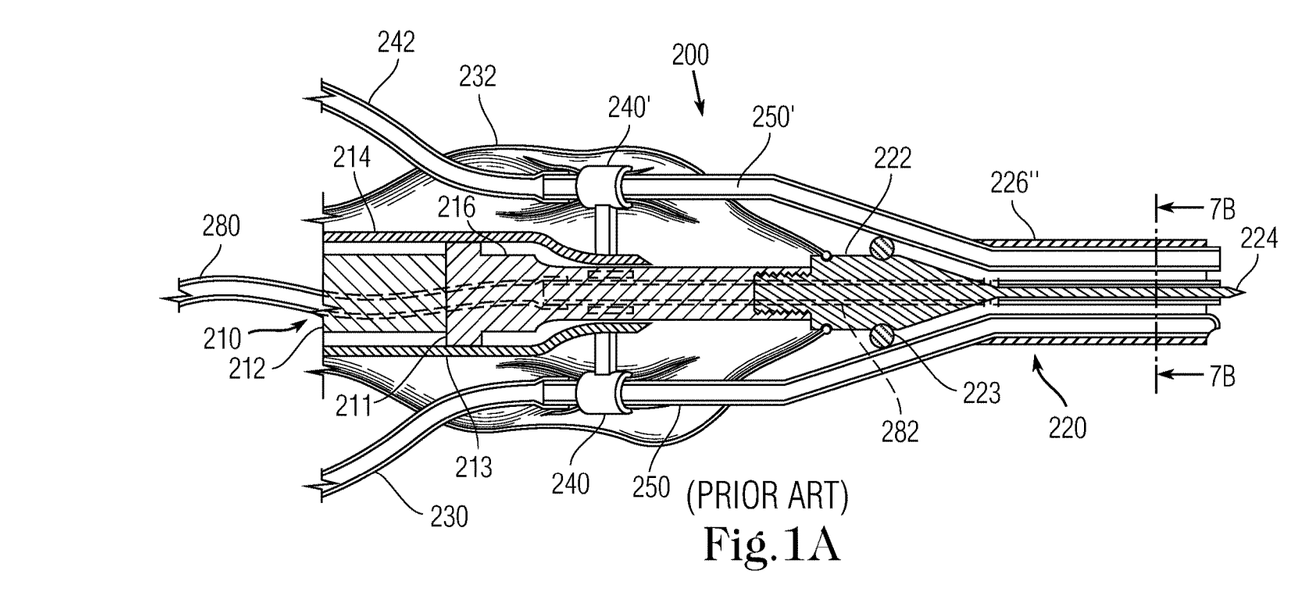
FIGS. 1A and 1B are a side view and a cross-sectional view, respectively, of a prior art surgical hand piece with irrigation, aspiration and a third fluid flow path that can be used to augment either of the other two paths.
Figure 1B:
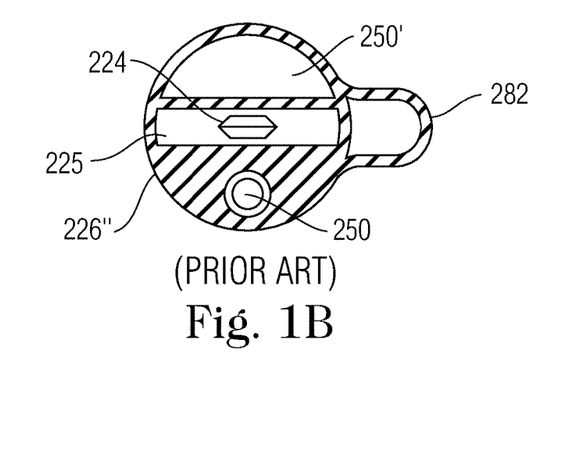

FIGS. 1A and 1B show a work tip for a prior art ultrasonic hand piece as shown in U.S. patent application Ser. No. 15/783,806 filed Oct. 13, 2017 for Dr. William Banko, the present inventor. This design has a handpiece 200 with an ultrasonic vibration part 210 connected to a work tip 220. The vibration part has a housing 214. A transducer 212 is provided in part 210 for generating ultrasonic linear mechanical vibrations upon excitation with an alternating-current electrical signal. The transducer is supported within the housing 214 by flanges 211. A metal connecting body 216 having a reduced diameter distal end portion is attached to the transducer 212. The connecting body forms an acoustic impedance transformer for conveying the longitudinal vibrations of the transducer 212 for application to the operative working tip 220 connected to the distal end of the connecting body 216. Further, the housing has a part 213 that engages the connecting body 216 at a null point in its vibration to provide further support.

The work tip 220 has a hub 222 connected to the distal end of the connecting body 216. The distal end of the hub narrows down to form a solid knife or scalpel 224. Flexible tube 230 extracts aspiration fluid from a rigid plastic tube 250 that is located along the knife 224 in the assembled condition. Similarly, a flexible tube 242 provides irrigation fluid to a rigid plastic tube 250' that is located along the knife 224.

A sterile sheet 232 surrounds the vibration part 210, housing 214 and connecting body 216 to isolate them from the non-sterile conditions at the work tip 220. In this design the sheet 232 is attached to the hub 222 of the knife which is detachable from the connecting piece 216. As a result, after an operation the hub can be detached from the work piece and it, the knife and the sheet can be discarded as a one-use product. Since the vibration part 210, housing 214 and connecting body 216 did not come into contact with any tissue or fluids from the last patient and will not contact the tissue or fluids from the next patient, there is no need to sterilize these elements between operations on different patients. As a result, multiple operations can be conducted in a shorter period of time and at less expense.

Rigid tubes 250, 250' are captured in tube holders 240, 240' with the sterile sheet between them. That is, the holders are within the sheet and are not exposed to the operating environment. As shown in FIG. 1B there is a sleeve 226" around the knife 224. This sleeve has channels 250, 250' which are extensions of the plastic tubes 250, 250.' The space 225 for the knife 224 is adjacent to the channels so the knife is adjacent to the fluid channels but does not touch them. Further, sleeve 226" includes a third channel 282 that is located on the side of the work pieces while the irrigation tube 250' is on the top and aspiration tube 250 is on the bottom. The tubes are all located on sleeve 226". The proximal end of the blade channel 225 is blocked by an O-ring 223 so that fluid from the operating site does not pass through this channel of the work tip.

During an operation, the hub 222 and knife 224 of work tip 220 are longitudinally vibrated by the transducer 212. The tubes 250, 250' remain stationary and are supported with respect to the hub and knife by means of the O-ring 223 at the interface between the hub and the tubes. The surgeon places the work tip 220 within the eye and against the cataract tissue. The ultrasonic vibration of the knife 224 causes the cataract tissue to emulsify. During this process irrigation fluid, e.g., saline solution, is injected into the site from tube/channel 250' since flexible tube 242 is connected to a source of irrigation fluid which may be moved by gravity flow or a pump. Also, the emulsified tissue is removed from the site by aspiration through tube/channel 250 because flexible tube 230 is attached to an aspiration pump. The tube 282 can be used to assist either the irrigation or aspiration flow.

In FIG. 1B the aspiration channel 250 is small compared to the irrigation channel 250'. This can be balanced out through the use of channel 282 to augment aspiration. During an A/I clean up procedure after the cataract has been broken up into little pieces, a low aspiration force is needed to remove the remaining pieces of lens and lens epithelial cells while preventing the tearing of the capsular bag of the eye. Under those circumstances the channel 282 can be closed or used to augment irrigation so that aspiration only occurs though channel 250.

The cross section shown in FIG. 1B has the channel 282 protruding from one side of sleeve 226". Since this structure is required to pass through an incision in the eye, it would be beneficial if the cross section were more uniform but provided the same functional benefits.

Further, there is a prior art work tip known as the "Cobra" tip that has a cone shape. In particular, a cylindrical work tip has an area in which its diameter is increased going from the proximal to the distal end. An early discussion of this tip can be found in the article "New Phaco Tip Geometry Balances Power, Suction," *Ophthalmology Times*, Jul. 15, 1992, Vol. 17, No. 14. As reported in the article the shape concentrates ultrasonic energy within the tip, improving safety and efficiency. In effect the sloped walls of the cone shape provide additional force when the tip is vibrated at ultrasonic rates. See also, the article "Funnel-shaped tip Controls Ultrasound Energy during Phaco," *Ocular Surgery News*, Jul. 1, 1992, Vol. 10, No. 13. It would also be beneficial if the enhanced performance of the Cobra tip could be incorporated into more modern work tips.

SUMMARY OF THE INVENTION

In accordance with the invention a surgical hand piece is provided with a solid ultrasonic knife or scalpel located in a sleeve with multiple fluid channels, while retaining a uniform cross section. Further, a cobra cone shape is incorporated into the distal end of the knife to improve it efficiency In an illustrative embodiment the surgical hand piece has a solid knife located within a circular sleeve. The sleeve provides irrigation and aspiration channels. Further, the knife may be located in its own channel and may be used to divide that channel into separate irrigation and aspiration fluid flows.

A cone shape may be included at the distal end of the knife. This cone shape in one embodiment interacts with structure within the sleeve so that in an extended state the work tip performs phacoemulsification, while in a retracted state the aspiration fluid flow path is altered to reduce the flow so that the same work tip can be used for irrigation/aspiration (I/A) clean up.

In another embodiment, the cone shape tip can be replaced with a cap shape that is open toward the distal side, which generates greater phacoemulsification energy than the cone shape.

A further embodiment has a work tip extending from a sleeve, where a portion of the work tip is in the form of a structure with a half cylindrical main part and a half hemispherical distal end. This structure is provided on the upper surface of a blade. The distal end of the structure has an aspiration cleanup hole in it. During phacoemulsification the blade engages the cataract, irrigation fluid flows out of the sleeve over the upper surface of the blade and around the attachment. Aspiration fluid flows through a collar located under the blade and into the sleeve. During cleanup, the work tip is withdrawn into the sleeve and fluid flow is reversed. In particular, aspiration occurs only through the clean up hole in the hemispherical distal end and into the sleeve above the blade. Irrigation fluid passes out of the sleeve under the blade and through the collar.

The principles of the invention have numerous advantages. For example, the invention allows for a work tip that is easier to insert into an incision in the eye, but still provides multiple fluid flow paths for use in phacoemulsification and clean up procedures. It also provides a cone shape to improve the efficiency of the ultrasonic vibrations. By causing the cone shape to interact with a structure in a surrounding sleeve, the work tip function can be changed from phacoemulsification to clean up without having to remove the work piece from the surgical site, such as the eye, and to replace it with an (I/A) clean up tool. Further, according to the present invention, clean up can be commenced without the surgeon having to divert his attention from the eye of the patient.

BRIEF DESCRIPTION OF THE DRAWINGS

The foregoing and other objects and advantages of the present invention will become more apparent when considered in connection with the following detailed description and appended drawings in which like designations denote like elements in the various views, and wherein.

DETAILED DESCRIPTION OF THE INVENTION

Figure 2:
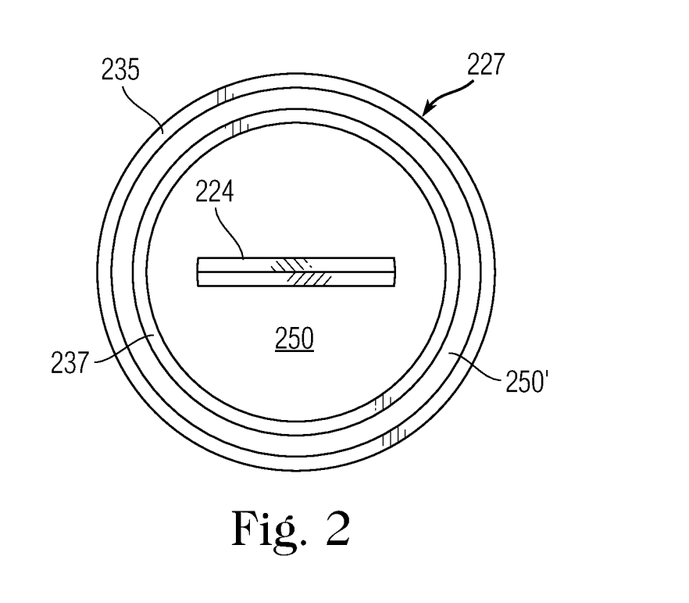
FIG. 2 is cross-sectional view of a blade within an inner channel of a work tip sleeve and a surrounding outer channel according to an embodiment of the present invention.

FIG. 2 shows an external sleeve 227 in the form of two concentric tubes 235, 237. The blade 224 is in the center of channel 250 but does not extend completely across the tube 237. With this arrangement irrigation fluid can flow in the channel 250' between the tubes, while aspiration fluid can flow in channel 250 within tube 237.

Figure 3:
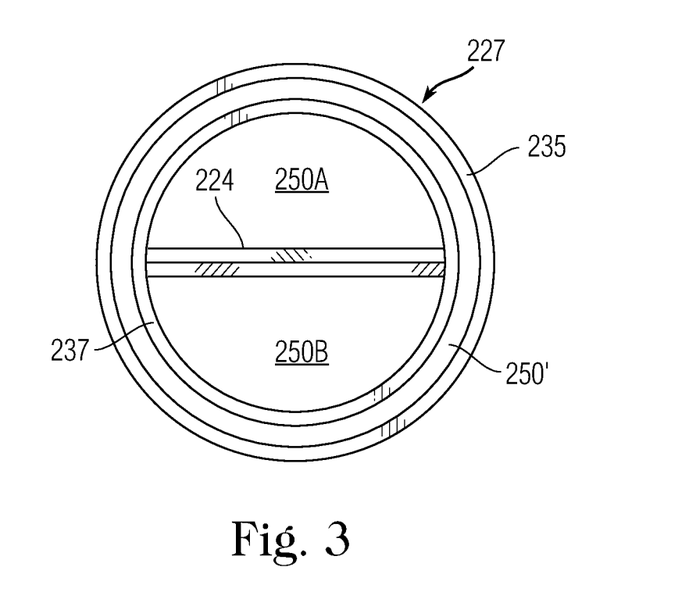
FIG. 3 is a cross-sectional view of a modification of the design of FIG. 2 in which the blade extends completely across the inner channel and divides it into upper and lower channels.

In FIG. 3 the blade 224 extends completely across tube 237 and separates the channel 250 into two distinct chambers, 250A and 250B. Again, the irrigation is in channel 250' between tubes 235, 237. However, because channel 250 has been divided into two channels, there are a total of three channels available that can be alternated or switched by the operation to change the performance. For example, the arrangement can have two aspiration channels and one irrigation channel, or one aspiration channel and two irrigation channels. It should be noted that in FIGS. 2 and 3 the sleeve 227 has a round shape which will make it easier for the surgeon to pass it into an incision in the patient's eye. In particular, it does not have a protrusion like channel 282 in FIG. 1B.

Figure 4A:
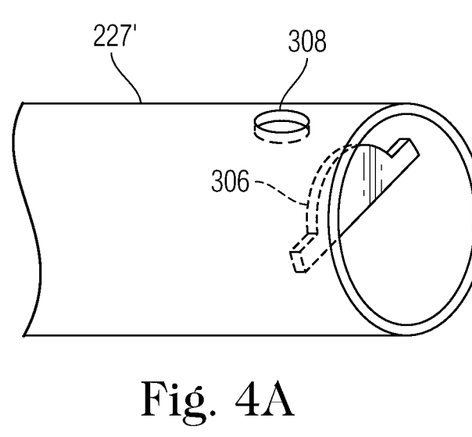
FIG. 4A is a right-side perspective view of the sleeve with an internal structure and hole near its distal end according to an embodiment of the present invention.
Figure 4B:
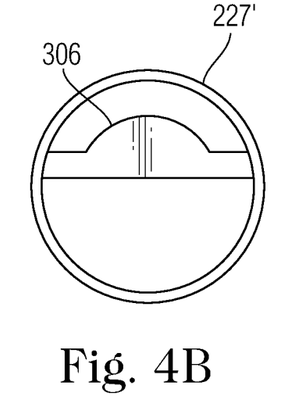
FIG. 4B is a front elevation view of the sleeve and structure of FIG. 4A

In FIG. 4A there is shown a small hole 308 in a single wall sleeve 227'. Because this sleeve has only a single wall, it cannot provide an outer irrigation channel. Instead, the single channel will need to be divided into irrigation and aspiration channels. As will be described in more detail below, the hole 308 can be used as the aspiration opening during cleanup. A structure 306 is shown suspended in the end of sleeve 227' in the upper part. The shape of the structure is best seen in FIG. 4B. Also, the location of the structure with regard to the hole 308 can be determined in FIG. 4C.

Figure 4C:
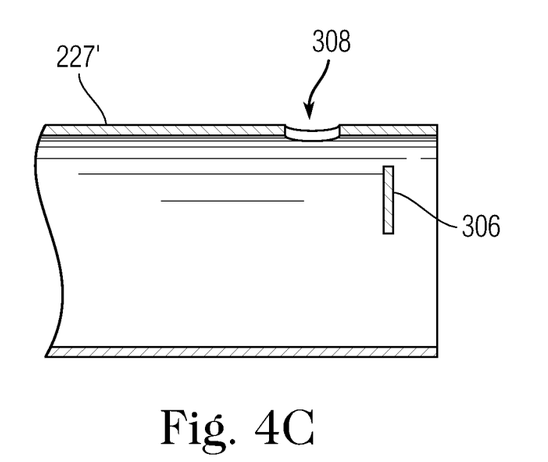
FIG. 4C is a right-side cross-sectional view of the sleeve and structure of FIG. 4A.
Figures 5, 6, 7, 8:
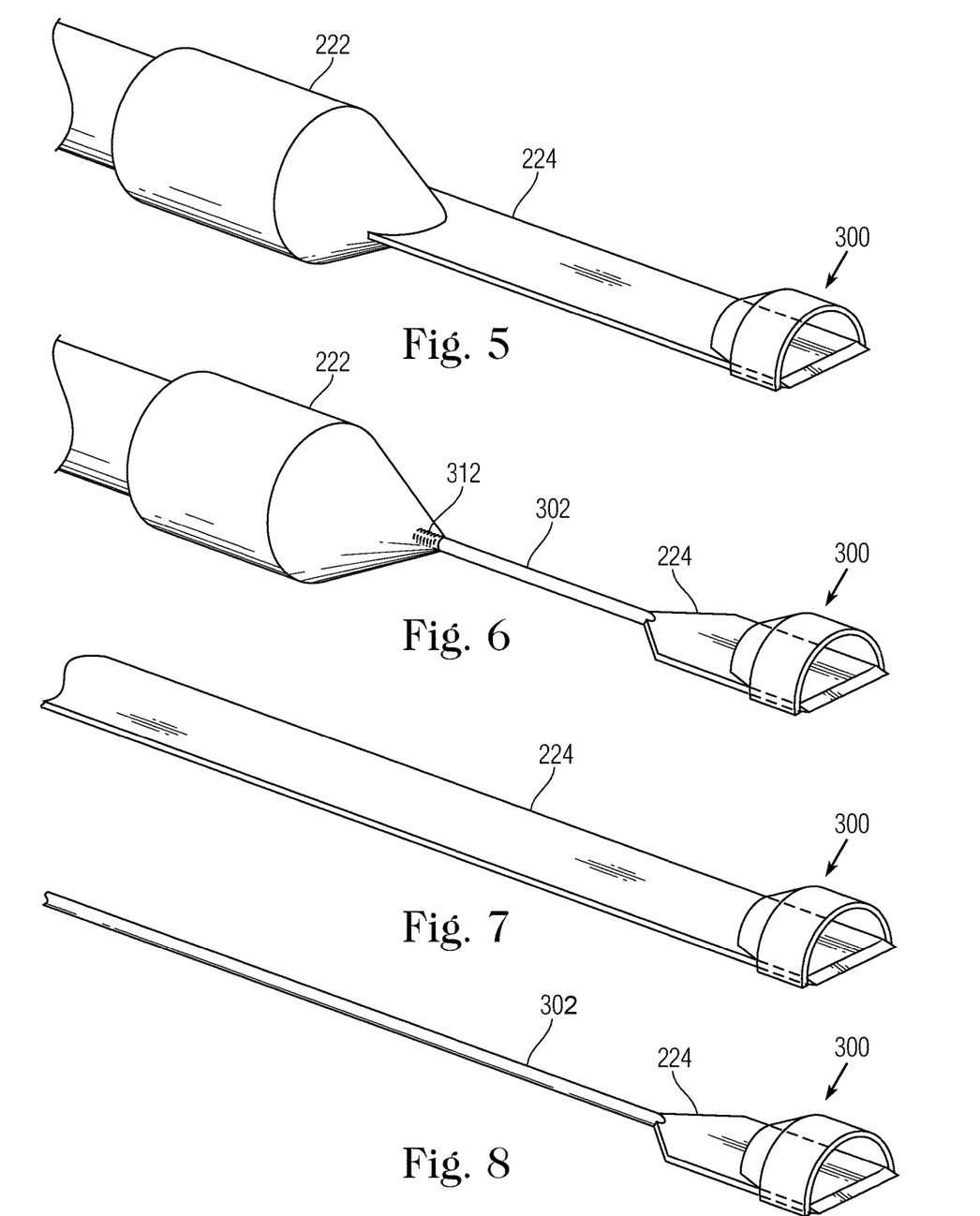
FIG. 5 is a perspective view of the connecting piece attached to a knife blade having a half conical structure at its distal end according to an embodiment of the present invention.
FIG. 6 is a perspective view of the connecting piece attached to a rod leading to the knife blade, which has a half conical structure at its distal end according to an embodiment of the present invention.
FIG. 7 a perspective view of a knife blade having a half conical structure at its distal end, but without showing a connecting piece according to an embodiment of the present invention.
FIG. 8 is a perspective view of a rod attached to a knife blade that has a half conical structure at its distal end, but without showing a connecting piece according to an embodiment of the present invention.
Figure 9:
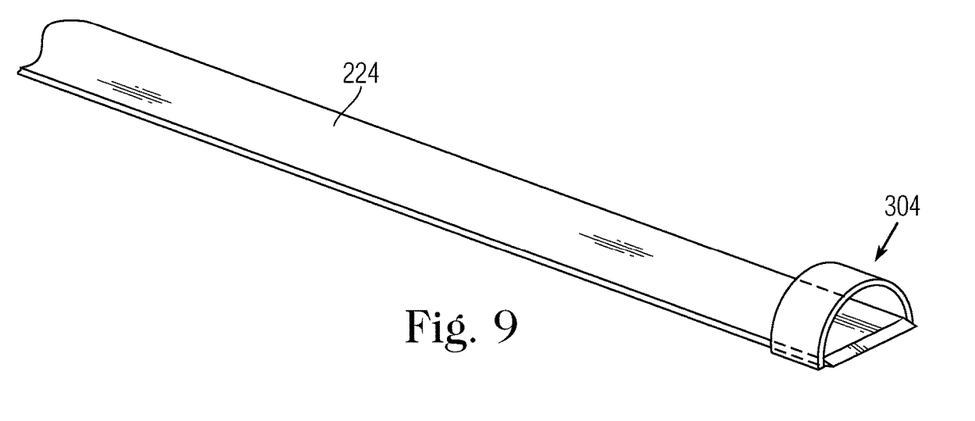
FIG. 9 a perspective view of a knife blade having a half ring structure at its distal end, but without showing a connecting piece according to an embodiment of the present invention.
Figure 10:
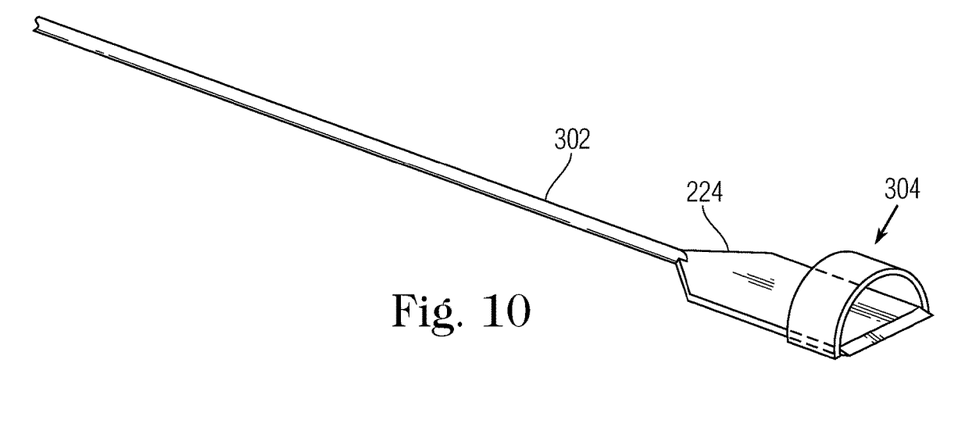
FIG. 10 is a perspective view of a rod attached to a knife blade that has a half ring structure at its distal end, but without showing a connecting piece according to an embodiment of the present invention.
Figure 11:
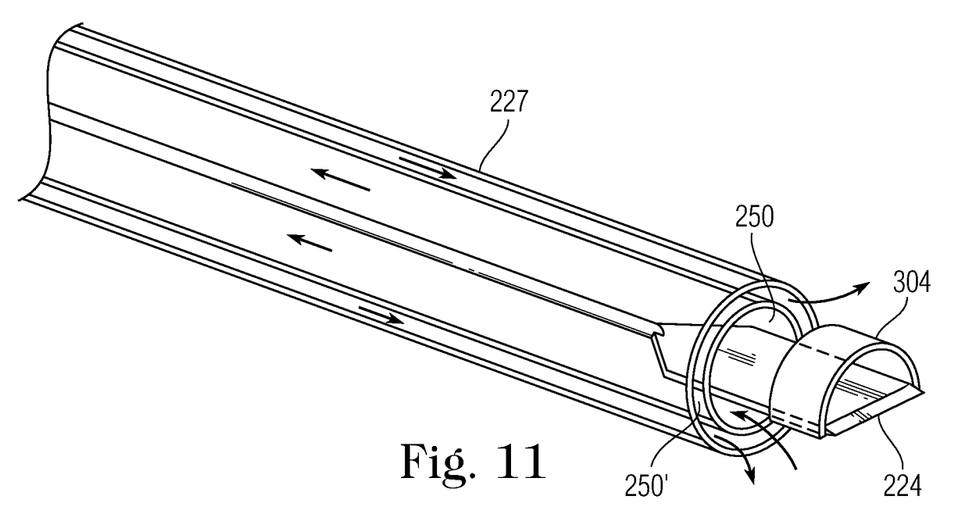
FIG. 11 is a perspective view of the distal end of a sleeve with irrigation and aspiration channels surrounding a rod with a knife blade at its end having a half ring according to an embodiment of the present invention.

The double wall sleeve 227 of FIGS. 2 and 3 or the single wall 227' of FIGS. 4A-4C is designed to be used with one of the knives shown in FIGS. 5-10, as shown, for example in FIG. 11. FIG. 5 shows a connecting body or hub 222 with a knife 224 extending from it. At the distal end of the knife there is a half Cobra tip 300, i.e., a cylindrical body with a conical shape at its proximal end. FIG. 6 shows the connecting body or hub 222 and a rod 302 extending from it to a portion of a knife 224. The connecting body and the rod are fixed to each other by a threaded connection 312. The distal end of the knife has half Cobra tip 300 fastened to it. The rod and connecting body or hub may be formed as one piece to lower the cost of machining the part. As an alternative the rod and/or blade may screw into the connecting body.

The design of FIG. 7 is similar to that of FIG. 5, but without the connecting body or hub. The design of FIG. 8 is similar to that of FIG. 6, but without the connecting body or hub. In FIG. 9 the design is like that of FIG. 7, but the half Cobra 300 is replaced with a half ring (collar) 304. In like fashion, the design of FIG. 10 is similar to that of FIG. 8, but with a half ring or collar 304.

In FIG. 11 the knife 224 of FIG. 10 is shown installed in the double-walled sleeve 227 of FIG. 3. The knife is vibrated at ultrasonic frequencies to break up the cataract. During this process irrigation fluid is directed to the surgical site through channel 250'. The emulsified tissue is withdrawn though channel 250, which also contains the knife. Note that the distal end of the knife has a shape edge for breaking the cataract. In addition, the distal edge of the collar 304 also impacts the cataract and assists in phacoemulsification.

Figure 12:
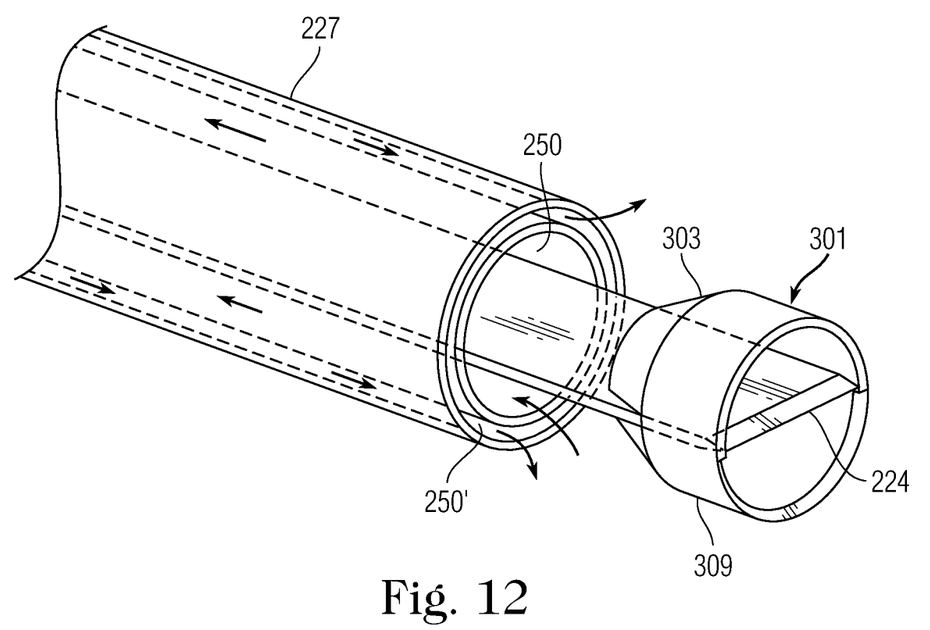
FIG. 12 is a perspective view of the distal end of a sleeve with irrigation and aspiration channels surrounding a knife blade with a full conical structure at its end according to an embodiment of the present invention.

The arrangement of FIG. 12 has knife 224 with a full Cobra tip 301 at its distal end. This knife is positioned in the sleeve 227 of FIG. 3. Generally, the design of FIG. 12 operates similar to that of FIG. 11. However, the full Cobra tip 301 increases the force generated by the ultrasonic vibrations. In particular, the conical shape 303 of the Cobra tip causes fluid to be pushed toward the surgical site. Also, note that in FIG. 11, aspiration fluid can be drawn into channel 250 both above and below the knife, and in particular under the ring 304. In the design of FIG. 12 if the cylindrical part 309 of the Cobra tip 301 has a diameter similar to the diameter of channel 250', no or at least a limited amount of irrigation fluid can pass from this channel, but aspiration fluid can flow though the full Cobra tip to enters the channel 250 after the tip. Since irrigation is important, the diameter should not be made large enough to limit irrigation flow In FIG. 13 there is shown the same knife as in FIG. 12, but the sleeve 227' is a single wall sleeve like that shown in FIGS. 4A-4C. The upper surface of the knife 224 slides under the bottom surface of the structure 306, which is in the distal end of sleeve 227'. The knife has a full Cobra tip 301 at its end. The conical wall 303 of the full Cobra tip forms an opening at the proximal end of the tip. The shape of this opening matches the shape of the structure 306 so that when the knife is withdrawn into the sleeve as shown in FIG. 14, the structure 306 blocks the portion of the opening at the proximal end of the tip that is located above the knife. The part of that opening below the blade is not blocked. As a result, irrigation fluid in the channel 250B can flow to the surgical site both when the knife is extended and when it is retracted.

Figure 13:
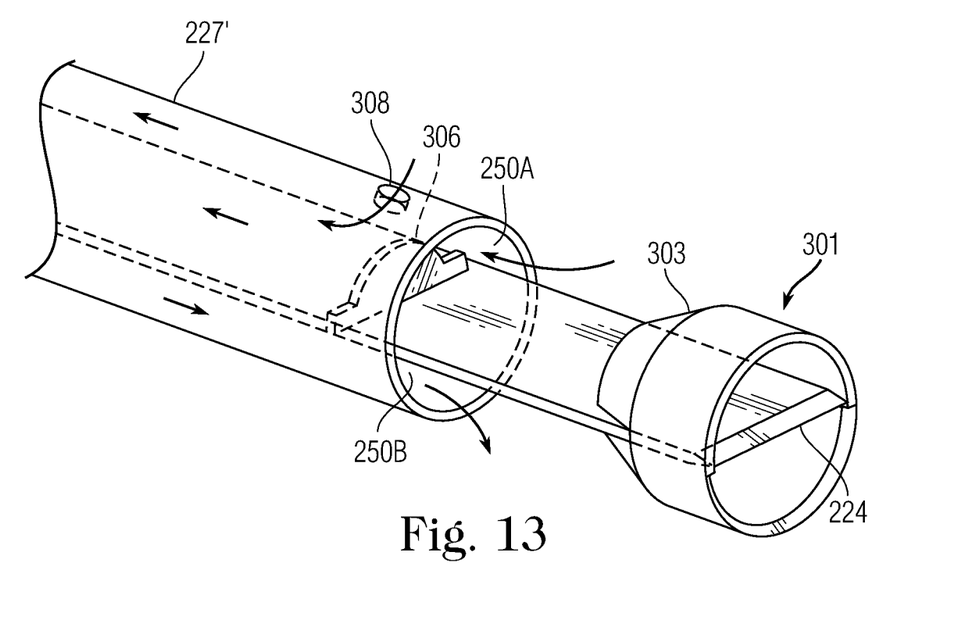
FIG. 13 is a perspective view of the distal end of a sleeve surrounding a knife blade in an extended state, a full conical structure at the end of the knife and a structure in the sleeve for changing the operation of the work tip according to an embodiment of the present invention.
Figure 14:
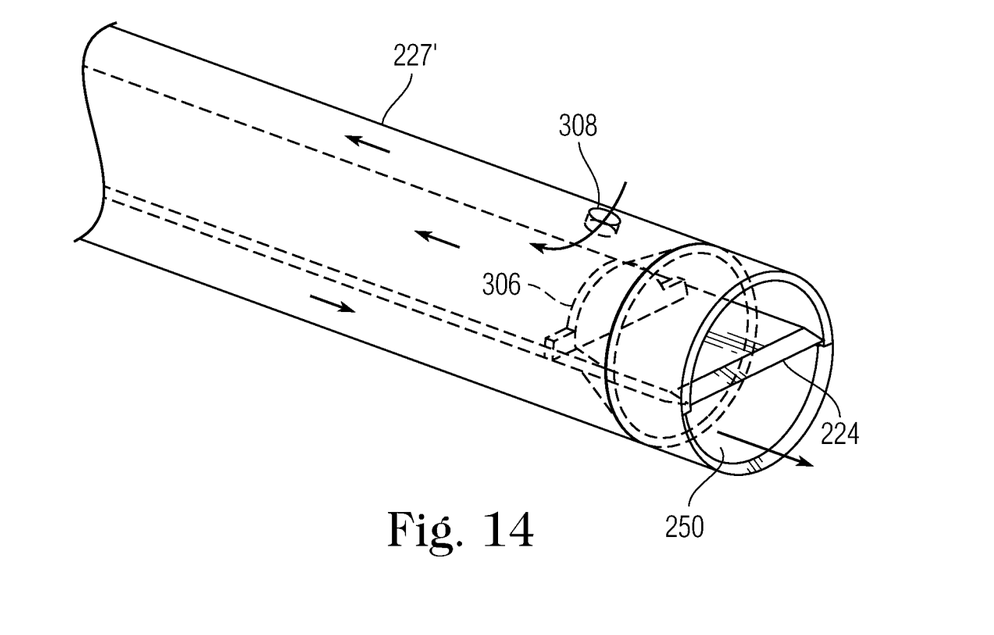
FIG. 14 is a perspective view of the arrangement of FIG. 13 with the knife in a retracted position.

The design shown in FIG. 13 with the knife extended is what is used for phacoemulsification. Aspiration fluid is withdrawn from the surgical site around and through the tip 301 and into the channel 250A above the knife. Also, a small amount of aspiration fluid flows through hole 308. When the tip is used for cleanup, the knife 224 is withdrawn into the sleeve 227'. The aspiration flow over the top of knife 224 and into chamber 250A becomes blocked by the structure 306, so the only path for aspiration is the reduced path through hole 308. Irrigation flow, however, can continue to flow through channel 250B.

Figure 15:
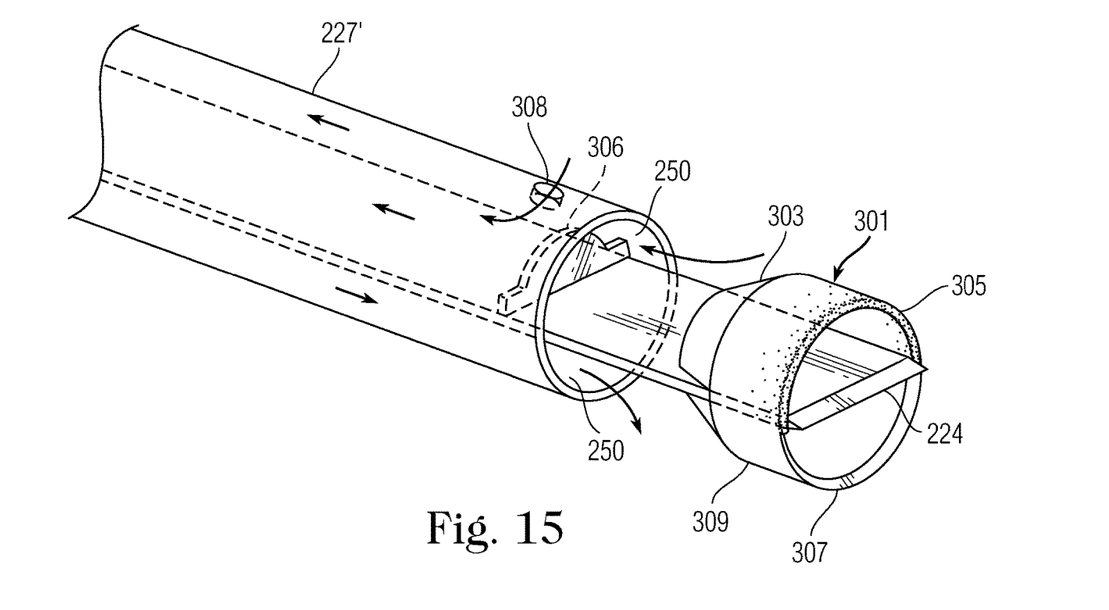
FIG. 15 is a perspective view of the arrangement of FIG. 13, but with an upper portion of the distal end of conical shape having a rounded textured surface and the lower portion being in the form of a sharp cutting edge.

FIG. 15 shows the same arrangement as FIG. 13, but an upper portion 305 of the distal end of the conical shape has a rounded textured surface and the lower portion 307 is in the form of a sharp cutting edge. The texturing of surface 305 can be achieved by several methods, for example by sand blasting. This textured surface is used to scrape the epithelial cells form the posterior capsule during the I/A procedure. The bottom half of the work tip with the sharp edge is used to cut the cataract.

Figure 16:
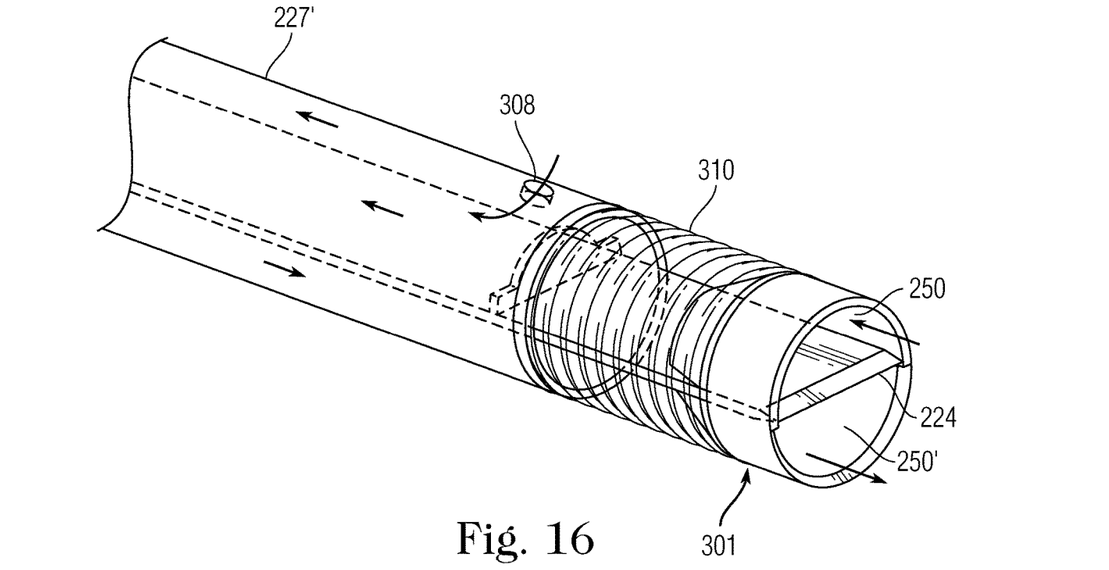
FIG. 16 is a perspective view of the arrangement of FIG. 13 further including a protective sheath between the distal end of the sleeve and the expanded part of the conical shape.

FIG. 16 shows the same perspective view of the work tip as shown in FIG. 13; but, equipped with a protective sheath 310 provided between the distal end of the sleeve 227' and the expanded or cylindrical part 309 of the conical/Cobra shape 301. Because of the sheath 310 fluid cannot flow around the Cobra tip but must go through the Cobra tip. The sheath can be thin, flexible and transparent.

Figure 17A:
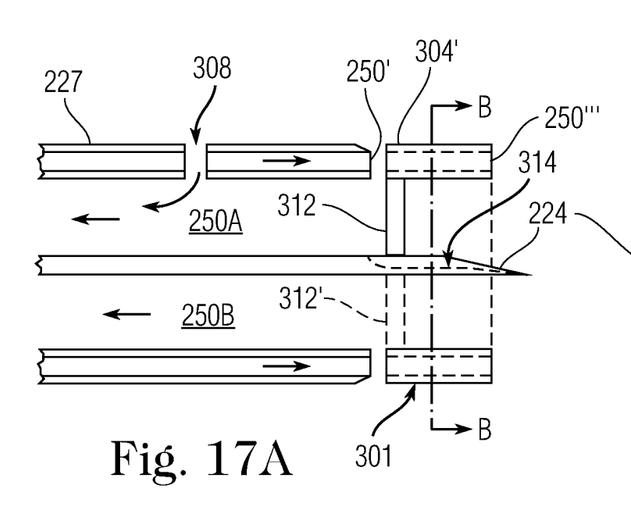
FIG. 17A is a side view of an arrangement similar to FIG. 11 but with a full ring and showing the blade surrounded by a sleeve with fluid irrigation channels and a radial blocking structure in the tip.
Figure 17B:
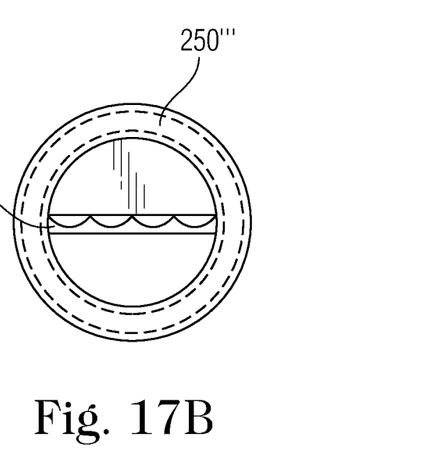
FIG. 17B is a front cross-sectional view along line B-B of the structure of FIG. 17A with the structure in the tip blocking the upper channel.

A side view of the arrangement of FIG. 11 with a collar 304 at the work tip is shown in FIG. 17A. A front cross-sectional view of this arrangement is shown in FIG. 17B. Unlike the structure of FIG. 11, in FIG. 17A the collar 304 extends completely around the knife 224, i.e., it is full collar 304'. Further, like the arrangement in FIG. 15, there is a structure 312 that blocks the channel 250A above the knife when the knife is retracted into the sleeve 227. However, the structure 312 is located at the proximal end of the collar and not within the sleeve. When the knife is extended, and a phacoemulsification operation is begun, the ultrasonic vibration of the collar breaks up the cataract. In addition, the vibration of wall 312 causes fluid cavitation that assists in breaking up the cataract. This perpendicular wall 312 is even more efficient in this respect than the conical wall 303 of a standard Cobra tip. The irrigation flow is in channel 250' during phacoemulsification and aspiration can be through channels 250A and 250B. During clean up, depending on the structure of collar 304', it can either block irrigation flow when the knife is fully retracted, or the collar can be provided with an extension of the channel 250''' so that irrigation fluid continues to reach the surgical site during clean up when the knife is retracted into the sleeve. In the fully retracted position the wall 312 blocks aspiration channel 250A, which tends to cause more aspiration to occur through hole 308, which can be ideal for cleanup. A similar wall 312' shown in dotted line can be provided on the tip 304' below the knife so as to block channel 250B and cause all of the aspiration to occur through hole 308.

Figure 18:
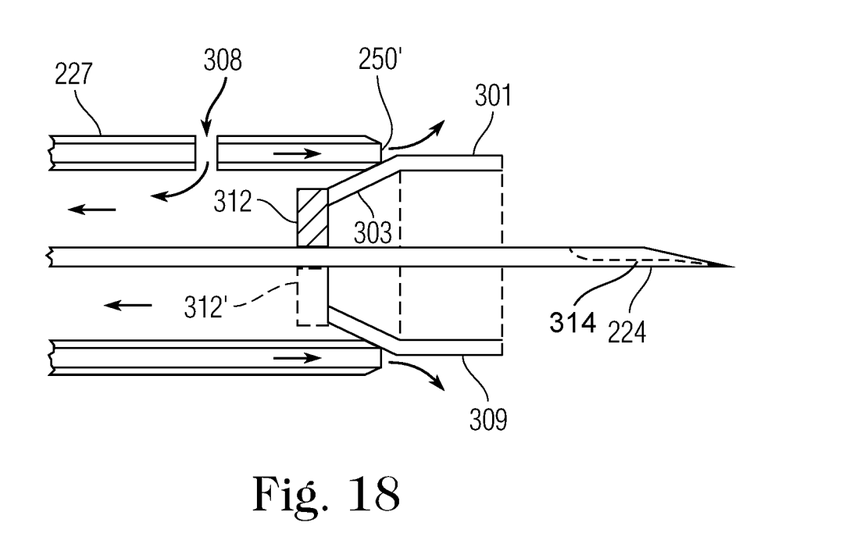
FIG. 18 is a side view of the structure similar to that of FIGS. 13 and 14 showing the blade and a structure within the sleeve blocking the proximal end of the cone shape.

FIG. 18 shows a side view of a schematic arrangement like that in FIG. 17A, but with a Cobra tip 301 instead of the collar 304. FIG. 18 shows the knife in the retracted position in which the opening at the proximal end of the conical surface 303 is blocked by the structure 312. As an option in this arrangement as well as in the arrangement of FIG. 17A, the cylindrical portion of the tip is smaller in diameter than the channel 250' so that even in the retracted position irrigation fluid can flow from channel 250'.

Figure 19:
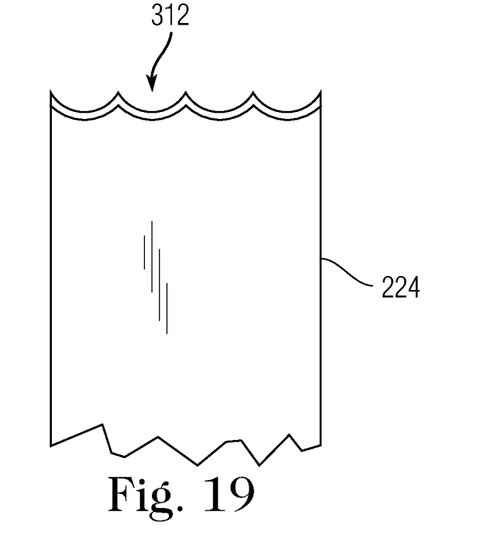
FIG. 19 is a plan view of a knife according to the present invention with a serrated edge.
Figure 20A:
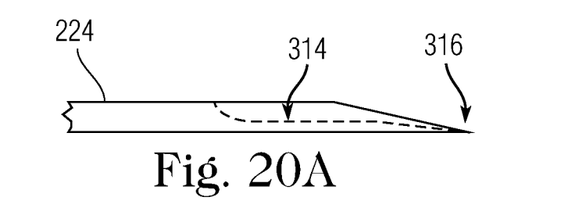
FIGS. 20A and 20B are side and plan views of a knife according to the present invention with scalloped edges.
Figure 20B:
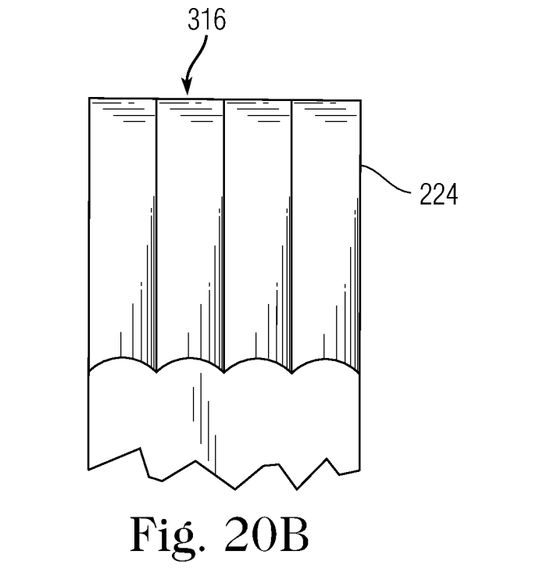

The end of the knife 224 in FIG. 18 shows a scooped portion 314 in dotted line that is shown in a side view in FIG. 20A and plan view in FIG. 20B. FIG. 19 is a plan view of the knife 224 with a serrated edge 316. This shape helps in the cutting of the cataract. As indicated FIGS. 20A and 20B are side and plan views of the knife 224 with scalloped edges. These edges also help with cutting of the cataract.

Figure 21A:
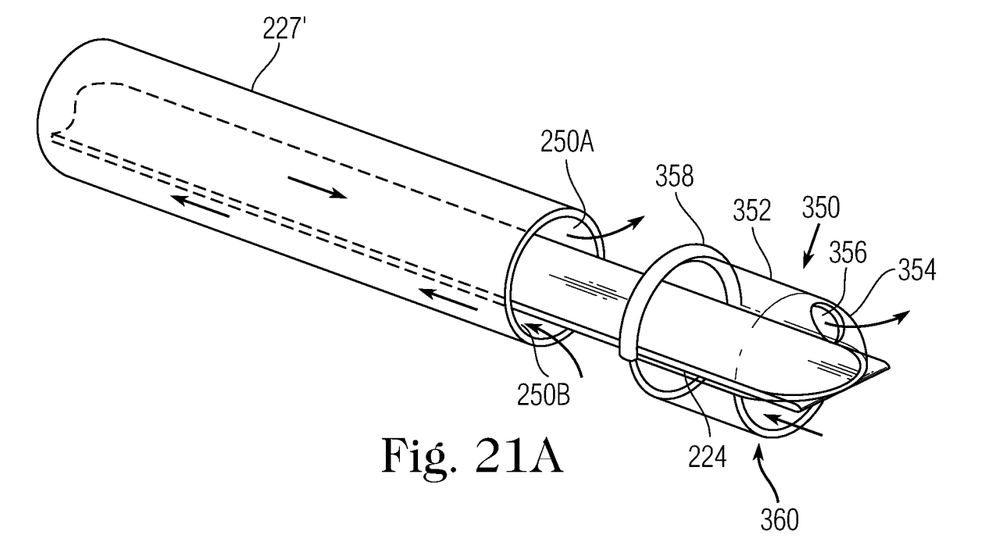
FIG. 21A is a perspective view of an embodiment with a work tip in the form of a half cylindrical/hemispherical structure on top of a blade and a collar below the blade, with the work tip in an extended position with regard to a sleeve.
Figure 21B:
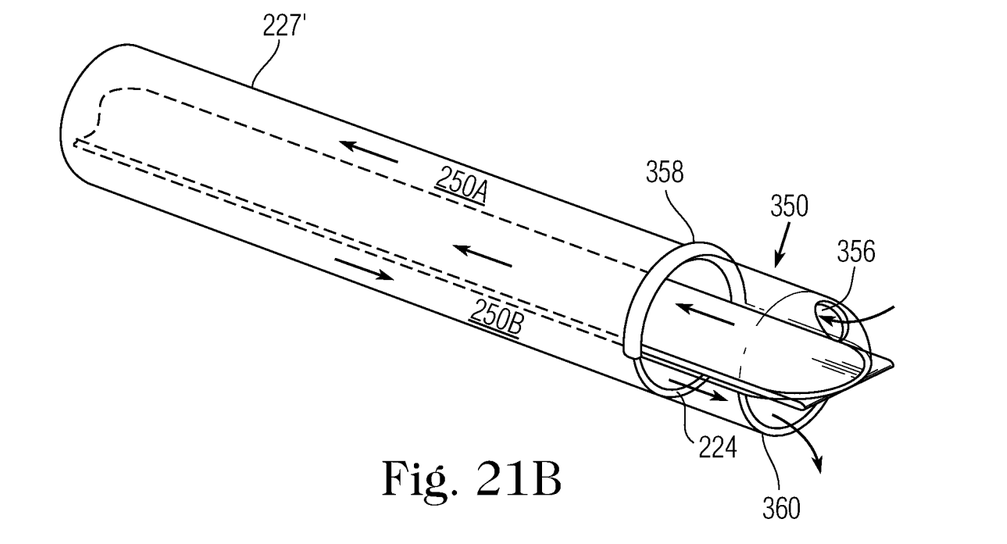
FIG. 21B is a perspective view of the embodiment of FIG. 21A in the retracted position.

FIGS. 21A and 21B show an embodiment with a work tip in the form of blade 224 that has a half cylindrical/hemispherical structure 350 on the upper surface of the blade. A half collar 360 is located on the lower surface of the blade at about the location of the half cylindrical/hemispherical structure 350. The structure 350 includes a half cylindrical part 352 and a half hemispherical part 354 that is on the distal end of the part 352. The part 354 has an aspiration hole 356. The proximal portion of the half cylindrical part 352 has a sealing member 358. During phacoemulsification, it is the distal edge of the collar 360 that scoops out or cuts the cataract. During cleanup, the instrument is turned over so only the smooth surface with the aspiration opening 356 that contacts the ocular sack.

The position shown in FIG. 21A has the work tip extended from the single walled sleeve 227'. If additional fluid flow arrangements were of interest, sleeve 227' could be replaced with a double walled sleeve 227 where fluid flow would exist between the walls as shown in FIG. 3. The embodiment of FIG. 21 is used for phacoemulsification when in the extended position of FIG. 21A. The portion of collar 360 below the blade 224 engages a cataract (not shown) while being vibrated at an ultrasonic frequency. This causes the cataract to break up into small pieces. During this time irrigation fluid passes through the sleeve from the hand piece (not shown) in the space 250A above the blade 224. It can exit the space between the distal end of the sleeve 227' and the structure 350, and flow around that structure to the surgical site. A portion of the irrigation fluid can also pass through hole 356 in structure 350 to the surgical site.

During phacoemulsification, the small pieces of cataract are aspirated by fluid flow into the sleeve through the space 250B. Pieces are drawn directly from the surgical site through the collar 360 and into the space 250B. In addition, some fluid is drawn from the space between the half cylindrical/hemispherical structure 350 and the distal end of the sleeve.

When it is time for irrigation/aspiration (I/A) cleanup of remaining epithelial cells on the capsular sack, the ultrasonic vibration may be reduced or turned off. Also, the work tip is withdrawn so that seal 358 engages the distal end of the sleeve above the blade as shown in FIG. 21B and closes off the flow of fluid above the blade and between the sleeve and work tip. In this state the fluid flow is reversed so that aspiration flow is set up in channel 250A. Thus, at the surgical site, aspiration occurs only through hole 356 on the rounded surface 354. This is much like a separate conventional I/A tool, but is part of a phacoemulsification tool, so 2 in 1 functionality is provided. During this I/A procedure, irrigation fluid is passed through channel 250B of the sleeve 227' below the blade 224, and through the collar 360 to the site of the cleanup.

The reversal of fluid flow can be by way of valves in the hand piece or the control apparatus as is well known in the art.

The work tip of FIGS. 21A & B can be made of metal, for example titanium. As an alternative, the half cylindrical/hemispherical structure 350 could be made of hard plastic or even some composite material that will withstand ultrasonic vibration, while the seal 358 is made of an elastomeric material.

Figure 22A:
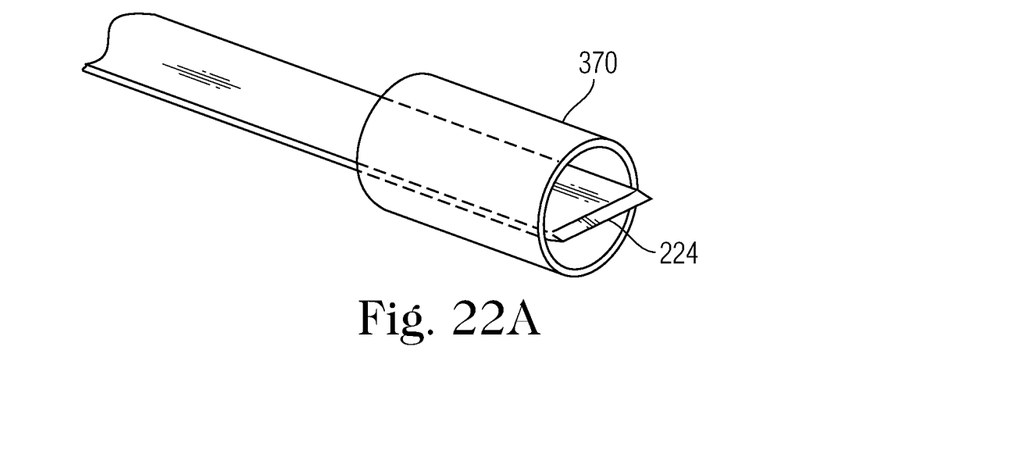
FIG. 22A shows a work tip with a full collar surrounding a blade.
Figure 22B:
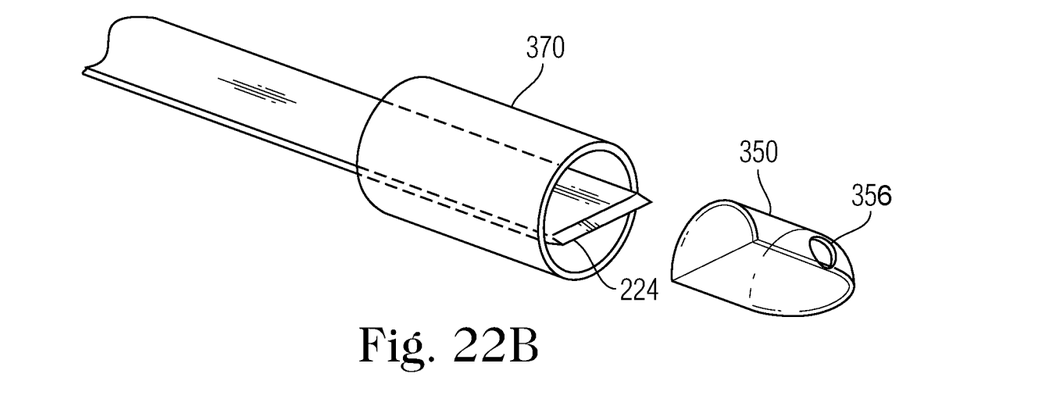
FIG. 22B shows a half cylindrical/hemispherical insert that fits in the collar of the work tip of FIG. 22A above the blade.
Figure 22C:
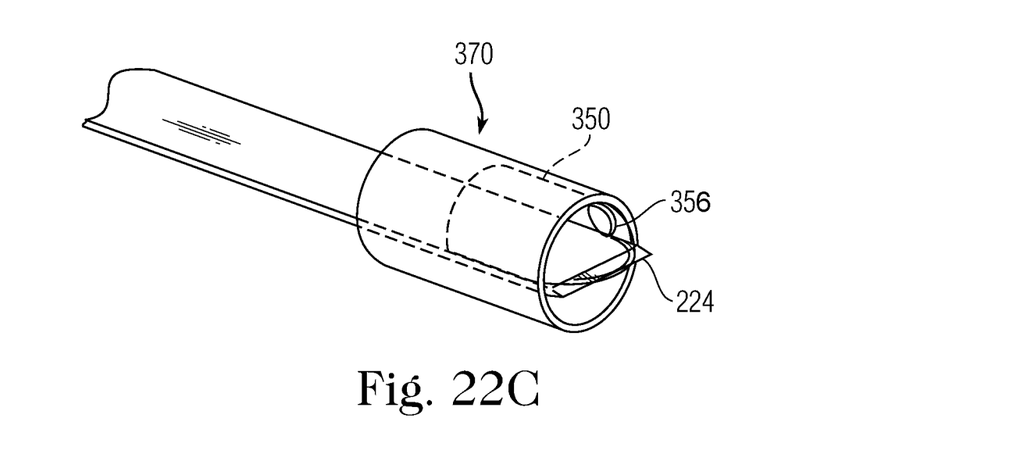
FIG. 22C shows the insert in position in the collar for operation according to the embodiments of FIG. 21.

FIG. 22A shows a work tip with a full collar 370 surrounding a blade 224. FIG. 22B shows the half cylindrical/hemispherical structure as a separate insert 350. This insert is adapted to fit in the collar 370 and be attached to the upper surface of the blade 224. FIG. 22C shows the insert 350 in position in the collar 370. When assembled in this way, the work tip of FIG. 22C can be operated similar to the embodiments of FIG. 21 discussed above.

While the invention has been shown and described in connection with the removal of a cataract from the eye of a patient and subsequent I/A clean up, the apparatus and method may also be used for other types of surgery in other parts of the body, e.g., the removal of neurological tissue.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the scope of the appended claims.

I claim:
1. A work tip for a surgical hand piece comprising:
 a solid knife with a flat distal end having a sharp distal edge within a plane of the flat distal end, said sharp distal edge extending from one side edge to another side edge of the flat distal end and being perpendicular to both side edges of the flat distal end, and said solid knife having its proximal end connected to a source of ultrasonic energy in the hand piece; and
 a sleeve having a generally uniform cylindrical shape, said sleeve surrounding the distal end of the knife, and providing available separate irrigation and aspiration fluid channels defined by opposite surfaces of the flat distal end of the knife that continuously provide irrigation and aspiration fluid during operation.

2. The work tip according to claim 1 wherein the knife has a conical tip at its distal end, said conical tip having a cylindrical portion connected to a conical wall that tapers to an opening so that there are proximal openings in the conical tip on both sides of the knife.

3. The work tip according to claim 2 wherein the knife is adapted to slide axially within the sleeve and the sleeve further includes a structure located within it that at least blocks a portion of the proximal opening in the conical tip on one side of the knife when the knife is slid so as to be withdrawn into the sleeve.

4. The work tip according to claim 3 wherein the sleeve further defines a hole adjacent to, but proximal of the structure so that when the proximal opening on one side of the knife is blocked, aspiration fluid flows through the hole to provide irrigation/aspiration clean up.

5. The work tip according to claim 3 wherein the distal end of the knife is in the form of a blade, portions of the conical tip with the cylindrical portion are on opposite sides of the blade, and the distal edge of the cylindrical portion on one side is textured and on the other side is sharp.

6. The work tip according to claim 5 wherein the structure blocks the conical tip on both sides of the blade when the knife is slid so as to be withdrawn into the sleeve.

7. The work tip according to claim 2 further including a connecting body connected to the knife, wherein said connecting body and knife form a single piece.

8. The work tip according to claim 2 further including a connecting body connected to the knife, wherein said connecting body and knife are attached to each other by a threaded connection.

9. The work tip according to claim 1 wherein the knife has a half collar tip at its distal end, said collar tip having a cylindrical portion connected to one surface of said knife.

10. The work tip according to claim 9 wherein the knife is a proximal rod connected to a distal flat blade with a shape end.

11. The work tip according to claim 1 wherein the knife has a half conical tip at its distal end, said half conical tip having a half cylindrical portion connected to one surface of said knife and a half conical wall that tapers from the cylindrical portion to a half opening on one side of the knife.

12. The work tip according to claim 1 wherein the knife is a rod with a blade at its distal end, a half collar tip being located at the distal end of the blade, said collar tip having a cylindrical portion connected to one surface of said blade.

13. The work tip according to claim 12 further including a connecting body at the proximal end of the rod, said rod being attached to the rod by a threaded connection.

14. The work tip according to claim 1 wherein the knife is a rod with a blade at its distal end, a half conical tip being located at the distal end of the blade, said half conical tip having a half cylindrical portion connected to one surface of said blade and a half conical wall that tapers from the cylindrical portion to a half opening on one side of the blade.

15. The work tip according to claim 1 further including a cylindrical part attached to and located at least partially about the distal end of the knife, and a protective sheath between the distal end of the sleeve and the proximal end of the cylindrical part.

16. The work tip according to claim 1 wherein the distal end of the knife is a blade, the blade has a full cylindrical collar surrounding and attached to the blade, and a wall blocking a proximal opening in the collar on at least one side of the blade so as to increase phacoemulsification.

17. The work tip according to claim 1 wherein the knife is a blade with a serrated edge.

18. The work tip according to claim 1 wherein the knife is a blade with scalloped edges.

19. The work tip according to claim 1 wherein the knife is a blade and further including a half cylindrical collar on one surface of the blade at its distal end, and a half cylindrical and half hemispherical structure through which the blade passes on the other surface of the blade adjacent the half cylindrical collar, an aspiration hole being provided in the half hemispherical structure for cleanup.

20. The work tip according to claim 19 wherein the knife can be slid into and out of the sleeve, and the half cylindrical and half hemispherical structure has a seal at its proximal end that moves therewith and engages the distal end of the sleeve and closes off a flow of fluid on that side of the blade as well as between the sleeve and the blade.

21. The work tip according to claim 19 wherein the cylindrical/hemispherical structure is separate from the blade and is inserted into the sleeve on one side of the blade when cleanup is performed.

\* \* \* \* \*